US009638689B2

United States Patent
Tong et al.

(10) Patent No.: US 9,638,689 B2
(45) Date of Patent: May 2, 2017

(54) INDIRECT ANTIGEN-SPECIFIC T CELL RECOGNITION ASSAY

(71) Applicant: Miltenyi Biotec GmbH, Bergisch Gladbach (DE)

(72) Inventors: Lan Tong, Cologne (DE); Peter Jahn, Cologne (DE); Mario Assenmacher, Bergisch Gladbach (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 271 days.

(21) Appl. No.: 14/201,519

(22) Filed: Mar. 7, 2014

(65) Prior Publication Data

US 2014/0256587 A1    Sep. 11, 2014

(30) Foreign Application Priority Data

Mar. 8, 2013    (EP) ..................... 13158357

(51) Int. Cl.
| | |
|---|---|
| *G01N 33/52* | (2006.01) |
| *G01N 33/50* | (2006.01) |
| *G01N 33/58* | (2006.01) |
| *C07K 14/705* | (2006.01) |

(52) U.S. Cl.
CPC ........... *G01N 33/52* (2013.01); *G01N 33/505* (2013.01); *G01N 33/5047* (2013.01); *G01N 33/5052* (2013.01); *G01N 33/582* (2013.01); *C07K 14/70596* (2013.01)

(58) Field of Classification Search
CPC .. G01N 33/52; G01N 33/5047; G01N 33/505; G01N 33/5052; G01N 33/582; C07K 14/70596
See application file for complete search history.

(56) References Cited

PUBLICATIONS

Kretschmer et al. Activated T cells induce rapid CD83 expression on B cells by engagement of CD40. Immunology Letters 136: 221-227 (2011)).*
Prazma et al. CD83 Expression Is a Sensitive Marker of Activation Required for B Cell and CD4+ T cell Longevity In Vivo. The Journal of Immunology Letters 179: 4550-4562 (2007)).*
Aerts-Toegaert, C. et al. (2007). "CD83 Expression on Dendritic Cells and T Cells: Correlation With Effective Immune Responses," *Eur. J. Immunol.* 37:686-695.
Breloer, M. et al. (2007). "CD83 is a Regulator of Murine B Cell Function in Vivo," *Eur. J. Immunol.* 37:634-648.

(Continued)

*Primary Examiner* — Gail R Gabel
(74) *Attorney, Agent, or Firm* — Morrison & Foerster LLP

(57) ABSTRACT

The present invention provides a method for analyzing simultaneously multiple human antigen-specific cell populations of a sample, the sample comprising B cells and antigen-specific cells, the method comprising a) separation of B cells from said sample, b) dividing the B cells into n sub-samples, c) differentially labeling the B cells of said sub-samples, wherein at least n-1 sub-samples are labeled, d) pulsing of the B cells of each sub-sample with single or multiple peptides, e) pooling of the labeled and peptide-pulsed B cells with cells of said sample comprising said antigen-specific cells, f) co-cultivation of the cells of step e), g) flow cytometry analysis of the B cells with regard to their cell number and CD83 expression, thereby determining the potency of said antigen-specific cells in said sample.

4 Claims, 13 Drawing Sheets

(56) References Cited

PUBLICATIONS

Breloer, M. et al. (2008; e-published on Mar. 7, 2008). "CD83 Regulates Lymphocyte Maturation, Activation and Homeostasis," *Trends in Immunology* 29(4):186-194.

Hirano, N. et al. (Feb. 15, 2006; e-published on Oct. 20, 2005). "Engagement of CD83 Ligand Induces Prolonged Expansion of CD8+ T cells and Preferential Enrichment for Antigen Specificity," *Blood* 107(4):1528-1536.

Kretschmer, B. et al. (2009). "Engagement of CD83 on B Cells Modulates B Cell Function In Vivo," *The Journal of Immunology* 182:2827-2834.

Kretschmer, B. et al. (Aug. 15, 2007). "CD83 Modulates B Cell Function In Vitro: Increased IL-10 and Reduced Ig Secretion by CD83Tg B Cells," *PLoS One* 8(e755):1-11.

Lüthje, K. et al. (Jun. 10, 2008). "CD83 Regulates Splenic B Cell Maturation and Peripheral B Cell Homeostasis," *International Immunology* 20(8):949-960.

Monks, C.R.F. et al. (Sep. 3, 1998). "Three-Dimensional Segregation of Supramolecular Activation Clusters in T Cells," *Nature* 395:82-86.

Quah, B.J.C. et al. (2013; e-published on Oct. 30, 2012). "Fluorescent Target Array T Helper Assay: A Multiplex Flow Cytometry Assay to Measure Antigen-Specific CD4+ T Cell-Mediated B Cell Help In Vivo," *Journal of Immunological Methods* 387:181-190.

Sheehy, M.E. et al. (2001). "A Novel Technique for the Fluorometric Assessment of T Lymphocyte Antigen Specific Lysis," *Journal of Immunological Methods* 249:99-110.

Wu, C. et al. (Apr. 1, 2009). "Activated B Cells Carrying HBCAG Peptide May Serve as Antigen-Presenting Cells to Induce HBV-Specific CTL Response In Vitro," *Journal of Hepatology* 50(Suppl. 1):S216, one page.

Zhou, L.J. et al. (Jul. 15, 1992). "A Novel Cell-Surface Molecule Expressed by Human Interdigitating Reticulum Cells, Langerhans Cells, and Activated Lymphocytes is a New Member of the Ig Superfamily," *The Journal of Immunology* 149(2):735-742.

\* cited by examiner

INDIRECT ANTIGEN-SPECIFIC T CELL RECOGNITION ASSAY

CROSS REFERENCE TO RELATED APPLICATIONS

This application claims priority to European Application No. EP13158357.7, filed Mar. 8, 2013, incorporated herein by reference in its entirety.

FIELD OF INVENTION

The present invention relates generally to the field of immunology, in particular to a method for analyzing simultaneously multiple antigen-specific cell populations of a sample.

BACKGROUND OF THE INVENTION

T cells are the central organizers and effectors of the immune system and are responsible for effective immunity against pathogens and tumors as well as for keeping unresponsiveness (tolerance) against auto-antigens and harmless non-self antigens, such as food. To achieve this goal T cells are educated either during their early development in the thymus or later on in the periphery to acquire distinct effector functions, which can be stably inherited from a single cell to its progeny and in this way contribute to immunological memory. The type of effector function and specificity of a T cell population determines the outcome of the immune response and may therefore have high diagnostic or prognostic value for immune mediated diseases, infections or cancer. The type of T lymphocyte activation and differentiation into certain functional distinct populations is determined by co-stimulatory activation signals from antigen-presenting cells. Activation signals are represented by ligands for receptors of T lymphocytes. Said ligands are situated on the surface of the APCs, they are bound to the extracellular matrix or secreted by cells, as are the cytokines. However, in addition to antigen-specific activation by signals via the T cell receptor (TCR) and co-stimulating molecules, non-specific activation of T lymphocytes has also been described, e.g. via cytokines or lectins.

CD83 is preferentially expressed by DCs and serves as a marker for DC maturation (Zhou et al. 1992: J Immunol 149:735-742). Recently, it has been suggested that CD83 is involved in the regulation of B cell maturation, homeostasis and function (Breloer et al. 2007: Eur J Immunol 37:634-48; Kretschmer et al. 2007: PLoS 2:e755; Luthjy et al. 2008: Int Immunol 20:949-60; Kretschmer et al. 2009: 182:2827-34). Furthermore, results of several studies also noted important role of CD83 in T cell activation. Hirano et al have shown that membrane bound CD83 delivers a significant signal specifically supporting the expansion of newly primed naïve CD8 T cells (Hirano et al. 2006: Blood 107: 1528-1536). Consistent with this, lymphocytes from CD83−/−mice have shortened lifespans in vivo (Prazma et al. 2007: J Immunol 179:4550-4562). In addition, the transient overexpression of CD83 by immature and mature human DCs enhances their T cell stimulatory capacity (Aerts-Toegaert et al. 2007: Eur J Immunol 37:686-695).

In Kretschmer et al the authors provide evidence that activated murine T cells induce CD83 on B cells via CD40 engagement but independent of TCR/MHC binding and thus independent of antigen-specificity of T and B cells (Kretschmer et al. 2011: Immunology Letters 136; 221-227).

All those findings support the notion that CD83 has multiple confirmed functions in regulating immune system development and function.

The state of the art provides methods for the analysis of a T cell population after in vitro stimulation. Such methods are e.g. ELISPOT and intracellular cytokine staining (ICS). Visualizing cytokine producing cells with flow cytometry and ELISPOT technology has facilitated the accurate enumeration of antigen specific T cells producing different cytokines. However the dependency of stimulating the cells with antigen restricts these methods to a read out of one antigen per stimulation.

Another common technology is the p/MHC tetramer technology, which offers a great convenience to directly stain epitope specific T cells without need of any stimulation and has made it possible to perform direct phenotypic analysis of different T cells in the same culture. However this method is HLA type dependent, meaning that the HLA type of the sample T cells has to match the HLA type of the p/MHC tetramer conjugate used.

A novel method is the FTA T-helper assay to monitor murine CD4+ T cell-mediated B cell help in vivo using a multiplex high throughput assay. This assay utilizes a fluorescent target array (FTA), which is composed of spleenocytes labeled with numerous (>200) unique fluorescence signatures that can be delineated in a single recipient animal based on combination labeling with the three vital dye carboxyfluorescein diacetate succinimidyl ester (CFSE), CellTrace Violet (CTV) and Cell Proliferation Dye eFluor 670 (CPD). By pulsing different B cell populations in a FTA with titrated amounts of cognate MHC-II binding peptides, CD4+ T cell help could be assessed by measuring induction of the B cell activation markers CD69 and CD44 by antibody labeling and flow cytometry (Quah et al. 2013: J Immunol Meth 387: 181-190). In another setting of the method also killing of CD8 T cells is analyzed. The disadvantages of the FTA are the restriction to a mouse in vivo model and the necessity of immunizing the animal prior the assay. To distinguish between CD8 and CD4 T cell responses the authors use MHC I or MHC II restricted peptides. By using multiple peptides one could not distinguish between a CD8 or CD4 derived B cell activation or lysis. Finally the FTA is not applicable to a human system as also the activation marker CD69 and CD44 are not specific for an antigen dependent cell-cell contact of B cells with T cells.

Therefore, the demand for an improved method to analyze simultaneously multiple human T cell populations in one sample remains still unsatisfied.

All references cited herein, including patent applications and publications, are incorporated by reference in their entirety.

SUMMARY OF THE INVENTION

Surprisingly, it was found that the expression of the surface molecule CD83 on human B cells, pulsed with multiple peptides can be used as an indirect marker for the potency of antigen-specific cells recognizing these multiple peptides.

B cells of a sample such as whole blood or PBMC are separated, divided into sub-samples, and pulsed with an antigen peptide pool respectively. Afterwards, the B cells are labeled with a intracellular fluorescent dye resulting in labeled peptide-loaded B cells which can be analyzed in a flow cytometry.

The B cells are co-cultured with the antigen-specific cells, regularly T cells, of the sample resulting in peptide-specific interaction between B cells and antigen-specific cells.

After incubation the different B cell populations are analyzed with regard to their CD83 expression or ratio allowing an assessment of the sample according to the presence of antigen-specific cells, their potency to stimulate B cells and their cytotoxicity. The invention disclosed herein can be used in an indirect T cell recognition assay (ITRA). ITRA is not applicable to a mouse system, as we discovered that CD83 expression is induced by a matching antigen specific B cell T cell contact in only human but not in mouse.

BRIEF DESCRIPTION OF THE DRAWINGS

FIG. 1A: B cells were labeled with different ratios of fluorescence cell staining reagent and different peptides. So barcoded B cells were analyzed by flow cytometry. FIG. 1B: left diagram: Different PBMC samples were stimulated with indicated peptide pools and thereafter cells were analyzed for CD154 positive CD4 T cell frequencies via flow cytometry. right diagram: ITRA with CD4 T cells. FIG. 1C: Different barcoded and peptide loaded B cells as indicated were co-cultured with autologous CD4 T cells in one sample and thereafter CD83 expression (C) of each B cell population was analyzed by flow cytometry. FIG. 1D: left diagram: Different PBMC samples were stimulated with indicated peptide pools and thereafter cells were analyzed for IFNγ positive CD8 T cell frequencies via flow cytometry. right diagram: ITRA with CD8 T cells. B cells were co-cultured with CD8 T cells and thereafter relative killing of B cells was analyzed and calculated from the flow cytometry data. FIG. 1E: Differently peptide pulsed and barcoded B cells before (left) and after 24 h co-culture (right) with autologous PBMCs. The ratio of each B cell population is shown.

FIGS. 3 and 3B: Correlation of antigen specific CD8 T cells and cytotoxicity within an ITRA. FIG. 3B: Correlation of cytotoxic killing and antigen specific CD8 T cell frequency of 3 different donors. Antigen specific CD8 T cell frequencies were calculated and titrated based on the frequency of IFNγ secreting cells upon pp65 stimulation of PBMCs.

FIG. 5A. Isolation of IFNγ secreting T cells after stimulation with multiple antigens. Left dot plot negative fraction and right dot plot positive fraction. FIG. 5B: left diagram: Antigen specific T cells were analyzed for IFNγ secretion after stimulation with different antigens as indicated. After CSA T cells were cultured for recovery and the ITRA was performed from day 0 to day 2 as indicated FIG. 5C. Schema of a possible clinical application of ITRA in combination with a CSA.

FIG. 6A. Expression of CD83, CD23 and CD69 on B cells upon antigen specific stimulation. B cells of CMV positive donors were barcoded and pulsed with pp65 peptide pool (black bars) or left unpulsed (with bars). B cells were co cultured with B cell depleted autologous PBMCs and thereafter analyzed by flow cytometry for CD83 (upper diagram), CD23 and CD69 (lower diagram) expression. CD23 and CD69 was up regulated on both peptide loaded and unloaded B cell populations (FIG. 6A), but CD83 expression was specifically increased only on peptide loaded B cells. FIG. 6B. Correlation between CD83 expression on B cells and Ag specific CD4 T cell frequency within the ITRA. As in FIG. 3, pp65 specific CD4 T cells, determined by IFNγ were titrated as indicated frequencies to pp65 peptide pulsed B cells. After co-culture CD83 expression was analyzed by flow cytometry. FIG. 6C. CD83 signal intensity depends on the ratio of B and T cells. Peptide loaded and unloaded B cells were mixed 1:1 and co-cultured in different ratios with antigen specific T cells. CD83 expression was measured by flow cytometry.

FIG. 7A. Ag specific CD83 up-regulation on B cells by CD4 and CD8 T cells. CD4 or CD8 T cells of CMV+ donors were co cultured with autologous B cells and stimulated with pp65 peptide pool. FIG. 7B. Up-regulation of CD83 on B cells by cytokines. B cells were cultured with different cytokines as indicated and thereafter analyzed for CD83 expression by flow cytometry. FIG. 7C. CD83 expression on B cells upon cross linking of MHCI or MHCII. MHCI and MHC II was cross-linked by using biotinylated antibodies directed against HLA DR, HLA ABC, and streptavidin as indicated. CD83 expression analyzed by flow cytometry. FIG. 7D. PBMCs were cultured alone or with equal numbers of J558L cells, untransfected or transfected with CD40L. CD83 expression was analyzed after 6 h by flow cytometry.

DETAILED DESCRIPTION OF THE INVENTION

Unexpectedly, it was found that the expression of the surface molecule CD83 on human B cells can be used as an indirect marker for antigen-specific cells in a method for analyzing simultaneously multiple antigen-specific cell populations of a sample, the sample comprising B cells and other cells such as CD4+ cells, CD8+ cells, NK cells or any peptide MHC recognizing antigen specific cell.

Figure 6A:
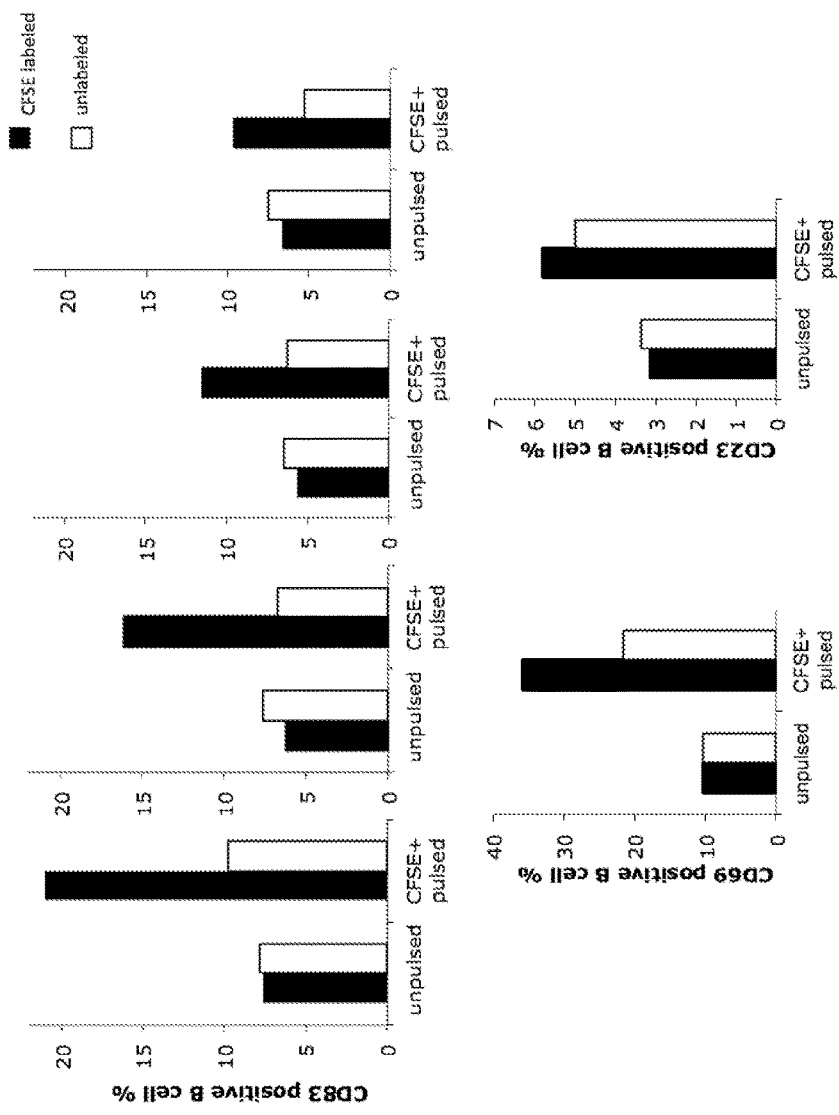
FIGS. 6A-6C: Peptide loaded B cells up regulate CD83 upon contact with Ag specific T cells.
Figure 6B:
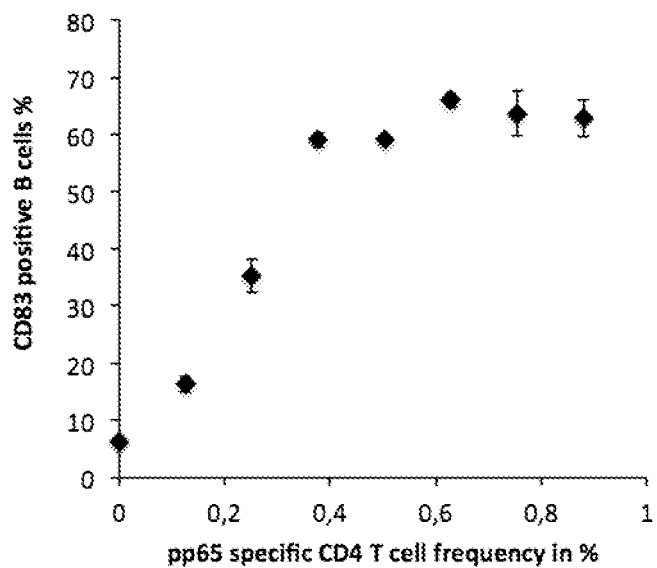
Figure 6C:
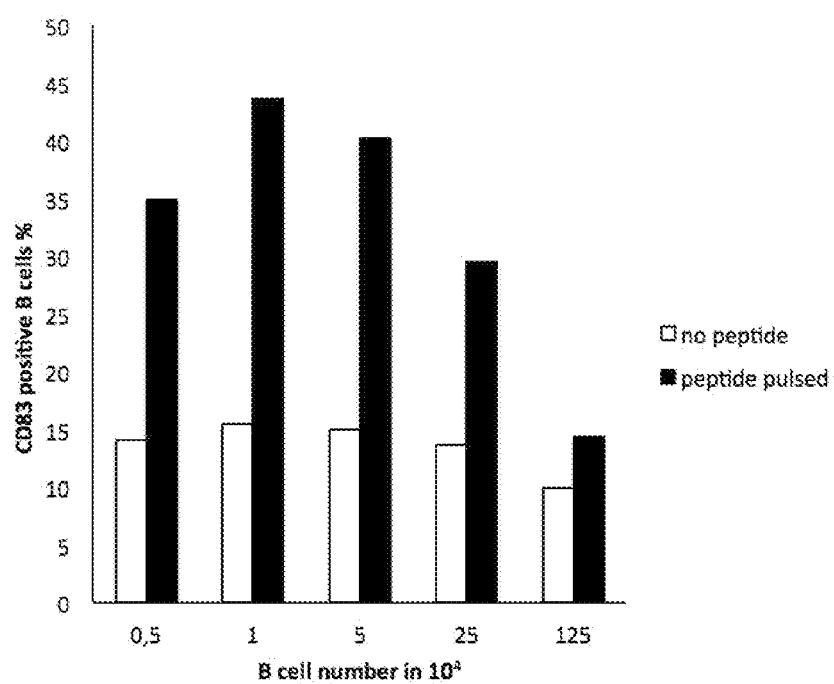

We loaded pp65 peptide pool on B cells and mixed them with equal amount of peptide free B cells from a CMV positive donor. B cell were co-cultured with autologous T cells and thereafter analyzed for CD83, CD23 and CD69 expression. Interestingly, CD23 and CD69 were up-regulated on both peptide loaded and unloaded B cell populations (FIG. 6A), but surprisingly, CD83 expression was specifically increased only on peptide loaded B cells. Thus CD83 up-regulation on B cells depends on antigen specific interaction with T cells and not on soluble factors in the culture. In addition, CD83 expression correlates to the frequency of antigen specific CD4 T cells (FIG. 6B). We could demonstrate a linear increase of CD83 expression with increasing CD4 T cell frequencies. However, at higher T cell frequencies CD83 expression reached a maximum. In order to avoid saturation, we identified the optimal ratio of B and T cells for co-culture (FIG. 6C). Collectively, the marker CD83 exhibits so far unknown properties as readout marker for an indirect T cell recognition assay for human samples comprising B cells and other cells.

Figure 7A:
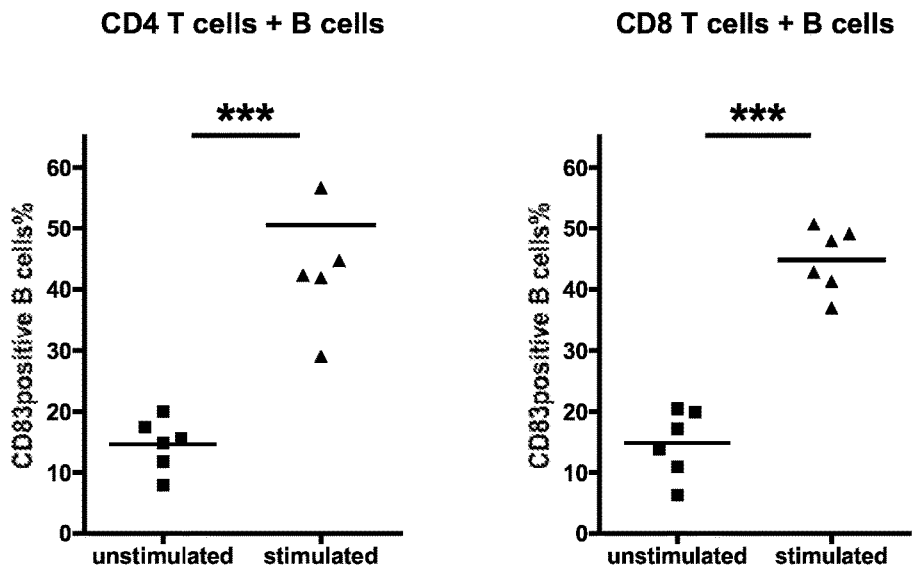
FIGS. 7A-7D. Mechanisms of CD83 up regulation on B cells.
Figure 7B:
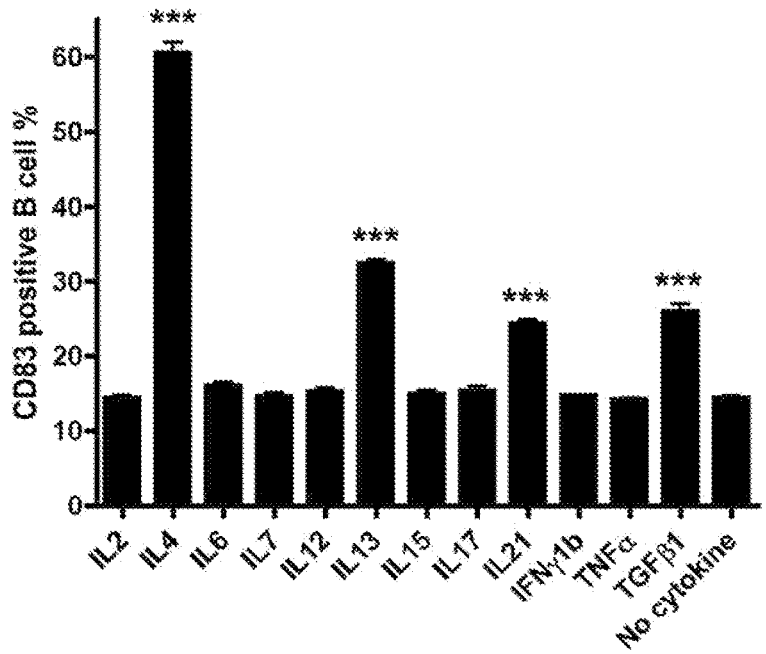
Figure 7C:
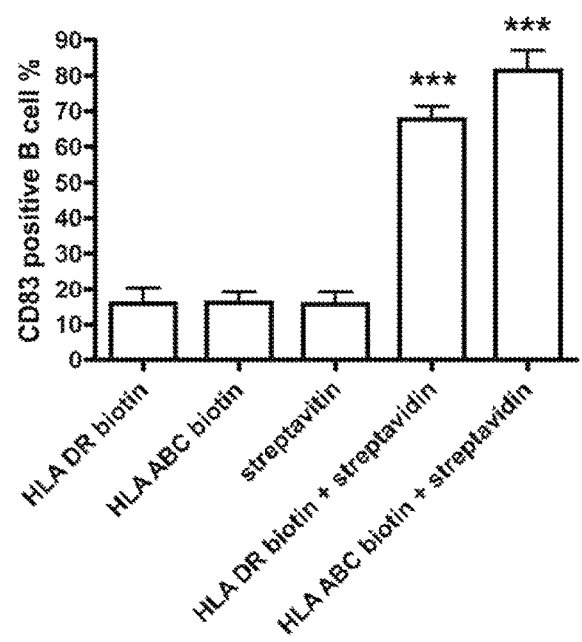
Figure 7D:
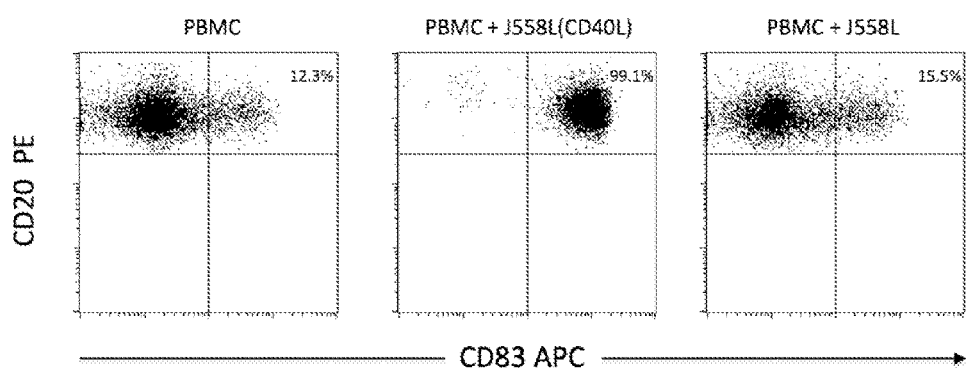

Recently CD83 was described as a sensitive marker of activation required for B cell and CD4 T cell longevity in vivo (Prazma et al. 2007: J Immunol 179:4550-4562). Interestingly, we observed that CD8 T cells are also capable to up-regulate CD83 on B cells upon stimulation, e.g. with CD40L (FIG. 7D). Our findings demonstrate that early events, for instance the accumulation of MHC molecules in an antigen specific recognition, as well as target directed cytokine secretion lead to CD83 up-regulation on B cells.

In our investigations we observed that interleucine 4 strongly induced CD83 on B cells 6 h after addition to the culture. Also IL13 and IL21 induced a slight increase of CD83 whereas other inflammatory cytokines like IFNγ or TNFα did not show an effect (FIG. 7B). It is known that cytokines can be secreted from effector-cell to their targets in a cell contact dependent manner, particularly IL-4 has been associated to be secreted into the immunological synapse of interacting T cells and APCs (Monks et al. 1998: Nature 395; 82-86). Moreover we observed other mechanisms involved in the T cell induced CD83 up-regulation on B cells. One occurrence in common during CD4 and CD8 activation is the recognition of MHC-peptide-complex via TCR and the formation of immunological synapse (IS). MHC-peptide complexes have been described to form clusters in the c-SMAC zone of the antigen presenting cells (APC). By antibody cross-linking of MHC molecules on B cells we observed strong CD83 up-regulation (FIG. 7C). Thus our findings suggest that early events, for instance the accumulation of MHC molecules in an antigen specific recognition, as well as target directed cytokine secretion and binding of CD40L lead to CD83 up regulation on B cells (FIG. 7D).

The recognition of target cells by cytotoxic T lymphocytes (CTL) is antigen-specific and restricted through the major histocompatibility complex (MHC). This facilitates the utilization of killing analysis to evaluate cytolytic activity of CD8 T cells with different antigen specificities in the same culture (Example 2). In our experiments cytotoxic lysis was observed specifically at the peptide loaded B cell population if both peptide loaded and unloaded B cells were co-cultured with autologous CD8 T cells. Relative killing correlates to the frequency of antigen-specific CD8 T cells in the culture (Example 2). The commonly established CD8 T cell detection based on IFNγ secretion or tetramer staining nicely quantifies the number of the antigen specific cells. However, this kind of quantification does not give enough information to estimate the ability of those antigen specific cells to execute their cytotoxic activity which is more relevant to the realistic outcome of virus or tumor clearance in vivo. We show that antigen-specific CD8 T cells from different donors possess different killing capacities at the same frequency. This observation confirmed the necessity to evaluate the immune potency of CD8 T cells in a more functional assay (Example 2). The method of the present invention combines the analysis of cytotoxic killing and CD83 expression on target B cells and discloses thereby a complete evaluation of antigen specific T cells.

The method of the present invention bases on cytotoxic killing and CD83 expression analysis observable after co-cultivation of the re-united labeled and peptide-pulsed B cells with other cells of the original sample. These other cells may be all remaining cells of the original sample excluding the separated B cells or these cells may be a specific population of cells generated by further separation of cells such as a population of CD4+ and/or CD8+ T cells. The two effects should be considered jointly resulting in the possibility of an assessment of the potency of the antigen specific T cells of the sample.

In general, three situations may occur using this method to evaluate antigen specific potency of T cells. A) Strong cytotoxic activity: Extensive killing of target B cells. B cell numbers are used to evaluate cytotoxic potency. B) Low cytotoxic activity: Moderate killing of target B cells. B cell numbers and ratio of CD83 expression on survived target B cells is used to evaluate T cell potency. C) No cytotoxic activity: Ratio of CD83 expression on target B cells is used to evaluate antigen specific potency of T cells.

If T cells are not specific for target B cells neither killing nor CD83 expression will occur and the sample is judged negative for that antigen.

Regularly, B cells up-regulate the surface marker CD83 shortly after isolation but then down-regulate this marker in cell culture. Pulsing of the B cells with multiple peptides and co-culturing these cells with the T cells of the original sample lead in a renewal and further up-regulation of the marker CD83 on the B cells. The effect of CD83 expression may vary depending on T cells chosen to contact with the B cells. CD8 T cells have the tendency to lyse partially or in rare cases completely all B cells of the sample during co-cultivation. CD4 T cells have rather the tendency not to lyse the B cells after co-cultivation but some subsets also may lyse B cells (Example 3). In our assay we are able to detect both effects, the lysis of B cells or induction of CD83 expression on B cells in on sample for various antigens. The analysis of both effects may allow conclusions about the potency of the antigen specific T cells. As it is known that not the number but rather the effector activity of T cells rules the outcome of an immune response and immunity.

Surprisingly, it was found that NK cells are able to kill specifically B cells in the method of the present invention. Using ITRA we were able to easily demonstrate a phenomenon, which is controversy discussed in literature, the antigen specificity of NK cells. We set up an ITRA where we depleted all CD4 and CD8 T cells using CD3 MicroBead depletion and co cultured the remaining cells with peptide loaded B cells. Interestingly we still observed antigen specific killing of pp65 and BZLF1 peptide loaded B cells in two donors, whereas the other co cultured B cells, unloaded or loaded with other peptides where left unaffected within the same ITRA sample (Example 4). To evidence that killing of B cells was induced by NK cells, we used the same donors and depleted all T cells and NK cells via CD3 and CD56 MicroBead depletion. This time no killing occurred either of pp65, BZLF1 nor of other peptide loaded B cells.

Therefore, in one aspect the present invention provides a method for analyzing simultaneously multiple human antigen-specific cell populations of a sample, the sample comprising B cells and antigen-specific cells, the method comprising a) separation of B cells from said sample
b) dividing the B cells into n sub-samples
c) differentially labeling the B cells of said sub-samples, wherein at least n-1 sub-samples are labeled
d) pulsing of the B cells of each sub-sample with single or multiple peptides
e) pooling of the labeled and peptide-pulsed B cells with cells of said sample comprising antigen specific cells
f) co-cultivation of the cells of step e)
g) flow cytometry analysis of the B cells with regard to their cell number (lysis) and/or CD83 expression, thereby determining the potency of said multiple antigen-specific cells in said sample.

The potency of said multiple antigen-specific cells in said sample in step g) are determined by i) B cell numbers if extensive killing of target B cells occurs (strong cytotoxic activity), ii) B cell numbers and ratio of CD83 expression on survived target B cells if moderate killing of target B cells occurs (low cytotoxic activity), and iii) ratio of CD83 expression on target B cells if no cytotoxic activity occurs. This allows conclusions about the potency of the antigen-specific cells such as CD4, CD8, and NK cells.

The division of B cells of step b) should result in two or more sub-samples (n is at least two).

The optimal incubation time of pulsing the cells in step d) depends on the length of peptide fragments presented and cells selected. For ITRA with CD4 T cells a pulsing time of 1 hour is sufficient, whereas for ITRA with CD8 T cells such short pulsing times would acquire short peptides of 9 amino acid length. Using longer peptides increases pulsing time for CD8 T cells.

The optimal period for co-cultivation of the cells on step f) depend on the cells selected. Co-cultivation period may be preferentially between 1 and 48 for hours, more preferentially between 12 and 36 hours, most preferentially about 24 hours.

Optionally, additional to the separation of B cells from said sample (step b) said antigen-specific cell populations are separated into sub-populations of cells such as CD4 T cells, CD8 T cells or NK cells.

Figure 1A:
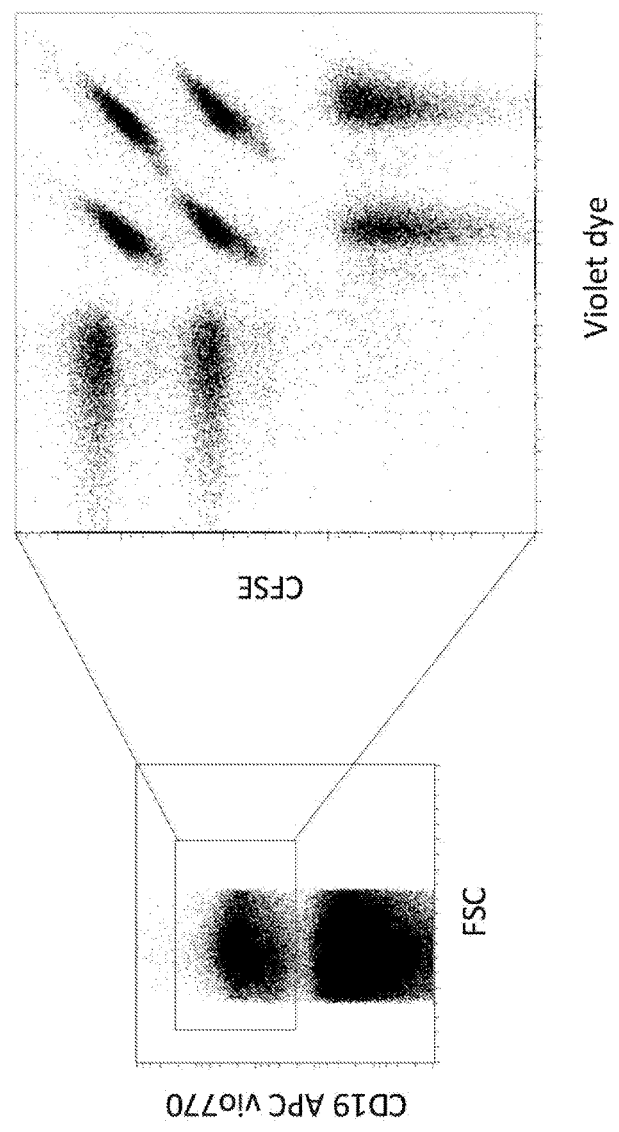
FIGS. 1A-1E: The Indirect T cell recognition assay (ITRA) analyzes in an antigen specific manner different T cell populations and their ability to activate or kill B cells in one sample.

The B cells of step c) are labeled with intracellular fluorescent dye such as carboxyfluorescein diacetate succinimidyl ester (CFSE), violet dye, or any other intracellular fluorescent dye known in the art. Several distinct populations of B cells can be acquired by flow cytometry using different combinations of cell dyes resulting in a multiplexing of the above described assay (see FIG. 1A).

Figure 5A:
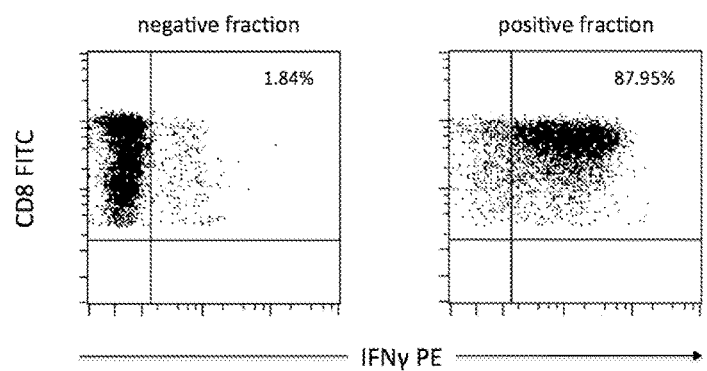
FIGS. 5A-5C: Functional characterization of multiple antigen CSA (cytokine secretion assay) isolated cells using ITRA.

This method, i.e. the assay can be used to analyze the potency of T cells to mediate a humoral response as CD4 T helper cells or mediate a cellular response as CTLs. Application for this assay would be e.g. the analysis of T cells in infectious diseases, cancer, autoimmune diseases and for evaluating the potency of adoptively transferred T cells as transplant (see FIG. 5).

Therefore, the invention may be used for obtaining information with prognostic or diagnostic value for certain diseases such as described herein.

Once the analysis of T cells of a donor has been performed and the T cells have been identified as antigen-specific for an antigen, the antigen-specific (T) cells of the donor can be used before and/or after cloning and/or growing and/or concentrated in cell mixtures and/or as pharmaceutical composition in the therapy or prevention of diseases. The pharmaceutical composition can be used for the treatment and/or prevention of diseases in mammals, possibly including administration of a pharmaceutically effective amount of the pharmaceutical composition to the mammal, preferentially to humans.

The disease may be any disease, which can be treated and/or prevented through the presence of a separated cell and/or through increasing the concentration of the relevant cells in/at the relevant place, or in whole mammalian subjects and/or patients. The cell may be for example an activated antigen-specific T cell, and the treated and/or preventively treated disease may be an autoimmune disease, an infectious disease, an allergy, transplant versus host disease (or allogeneic transplant rejection) and/or any other disease initiated by hypersensitivity. Diseases for which the use set forth in the invention is particularly suitable are those arising through and/or during a lack of regulation of the immune response. These diseases may be transplant rejections, allergic conditions, certain infectious diseases, tumors and/or autoimmune diseases.

DEFINITIONS

Unless defined otherwise, technical and scientific terms used herein have the same meaning as commonly understood by one of ordinary skill in the art to which this invention belongs.

The term "sample" as used herein refers to an B cells containing sample, e.g. whole blood, peripheral blood sample, leukapheresis harvest, buffy coat preparation, umbilical cord sample, and bone marrow aspirate. The samples can be from animals, especially mammals. Preferably, the samples are from humans.

The term "antigen-specific cells" as used herein refers normally to antigen-specific T cells but also includes NK cells which are found herein to be able to kill specifically B cells in the method of the present invention or to any other cell sub-population which may have antigen-specific properties. The term antigen-specific cells does not refer to the B cells.

Figure 3A:
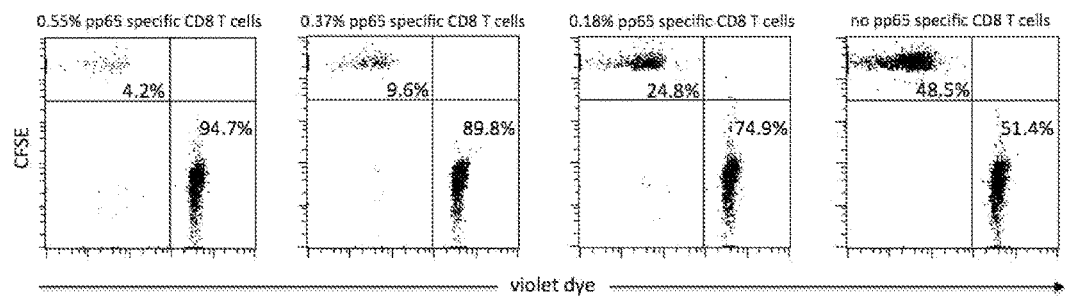
FIG. 3A: Titration of pp65 specific CD8 T cells to pp65 peptide loaded B cells in separate samples and analysis of cytotoxicity by flow cytometry.
Figure 3B:
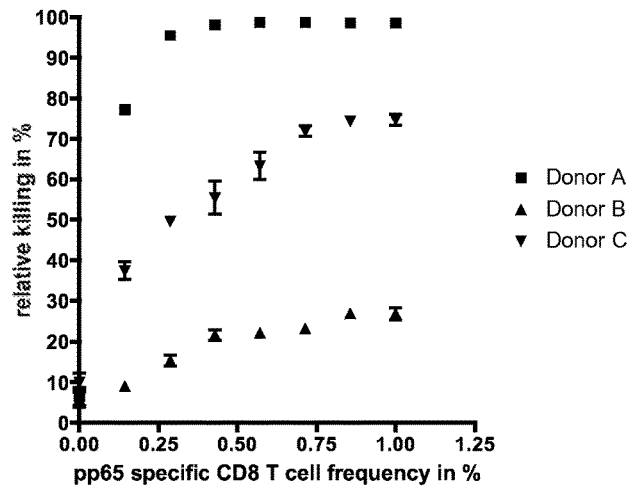

The term "potency" of an antigen specific T cell as used herein refers to the feature of an antigen-specific T cell to which scale it can kill or stimulate an antigen presenting cell. As shown in FIG. 3B the relative killing in % of pulsed and peptide loaded B cells by the antigen-specific T cell depends not only on the absolute cell number but also on the effectivity of the T cells to kill the B cells (different donors show different levels on relative killing). On the other hand the amount of CD83 positive B cells after co-culture with T cells depicts the potency of T cells to recognize antigen during cell-cell contact and their ability to stimulate B cells. In vivo this would lead to further activation and maturation of B cells and induction of a humoral immune response.

The term "stimulation" as used herein refers to a productive cell-cell contact, meaning that an antigen presenting cell like a B cell gets in contact with an antigen sensing cell like a T cell. The B cell presents a peptide MHC complex, which is scanned by the T cell receptor of the T cell. If the TCR recognizes the peptide MHC complex as its antigen, the T cell will intensify the cell-cell contact with pairing co-stimulatory receptors and ligand between both cells. This productive cell-cell contact leads to a stimulation of both, the B and the T cell.

If the TCR does not recognize any peptide MHC complex as its antigen, the cell-cell contact remains short and no stimulation will occur.

The term "peptide pool" as used herein refers to the mixture of overlapping peptides which cover the sequence of a protein antigen. E.g. the peptides consist of 15 amino acids and overlap 11 amino acids to the next peptide. The peptide pool should comprise the epitope(s) the T cells are specific for. For pulsing MHC II molecules the length of peptides is irrelevant. In contrast pulsing MHC I molecules the optimal peptide length is 9 amino acids, with longer peptides the pulsing time increases.

For ITRA we used peptide pools instead of complete antigens. The best way to generate antigen presenting B cells is the pulsing with peptides, as B cells are very poor in the uptake and processing of complete antigen proteins. Using peptides we avoid the necessity of phagocytosis and processing of antigen to generate peptide MHC complexes. During B cell pulsing peptides spontaneously bind to MHC molecules and build peptide MHC complexes extracellularly during cell pulsing.

The term "marker" as used herein refers to a cell antigen that is specifically expressed by a certain cell type or in a certain state of stimulation of a cell type. For example, CD83 is a surface marker for activated B cells. It is up-regulated after an antigen specific contact with e.g. an antigen specific T cell.

The term "target cells" as used herein refers to peptide pulsed or unpulsed B cells in or isolated of body fluids, as blood samples or PBMC of patients or healthy donors.

The term "untouched" as used herein refers to a negative magnetic selection of cells. Cells are labeled with magnetic particles which are not of interest and thus retained on the separation column, only the cell fraction that goes through is collected, as it contains the cells of interest. As these cells are non-labeled by an antibody coupled to micro- or nanoparticles, they are termed "untouched".

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Multiplexing is achieved by using different intracellular fluorescent dyes and different concentrations of these dyes resulting in a diversity of combinations resulting in differing labeled cells analyzable in flow cytometry. It is an advantage of the method of the present invention that multiplexing allows the analysis of different antigen-specific T cells from one sample. Only a small volume of the sample, e.g. whole blood or PBMC, is needed for parallel (simultaneous) analyses of the different antigen specificities of the B and T cells.

For enrichment, isolation or selection of cells, such as B cells, CD4 and CD8 T cells from a sample in principle any sorting technology known in the art can be used. Cells may be sorted by flow cytometry methods such as FACS sort.

Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack.

However, in a preferred embodiment for enriching, sorting and/or selecting cells from a sample containing B cells CD4 and CD8 T cells or other antigen specific cell types monoclonal antibodies are used in conjunction with colloidal superparamagnetic microparticles having an organic coating by e.g. polysaccharides (Magnetic-activated cell sorting (MACS) technology (Miltenyi Biotec, Bergisch Gladbach, Germany). These particles (nanobeads or MicroBeads) can be either directly conjugated to monoclonal antibodies or used in combination with antiimmunoglobulin, avidin or anti-hapten-specific MicroBeads.

The MACS technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s).

The B cells may be selected e.g. by using magnetic cell sorting technology by positive selection using anti CD19- or anti-CD20 antibodies (or fragments thereof) coupled to the magnetic micro- or nanoparticle. B cells may also be selected e.g. by using magnetic cell sorting technology by negative selection, e.g. a CD3/CD14/CD56/CD15 depleted sample.

CD4+ T cells may be selected e.g. by using magnetic cell sorting technology by negative selection, e.g. a CD8/CD19/CD56 depleted sample.

CD8+ T cells may be selected e.g. by using magnetic cell sorting technology by negative selection, e.g. a CD4/CD19/CD56 depleted sample.

Embodiments

In one embodiment of the invention B cells are isolated untouched from a sample such as PBMC, divided into several sub-samples (at least 2) and incubated with different peptide pools. To achieve a full CD8 response B cells have to be incubated with peptides for more than 2 h (optimal incubation time depends on the length of peptide fragments presented). In contrast, CD4 response already reached the maximum after 1 h of peptide pulsing. Using different combinations of cell dyes such as CFSE and violet dye, distinct populations of labeled B cells can be acquired by flow cytometry. The remaining cells of the sample (after separation of B cells) and the with different peptides loaded B cells are co-cultured (optimally for 24 h hours). Thereafter CD83 expression of each B cell population is measured by flow cytometry as exemplified in FIG. 1C.

Figure 1B:
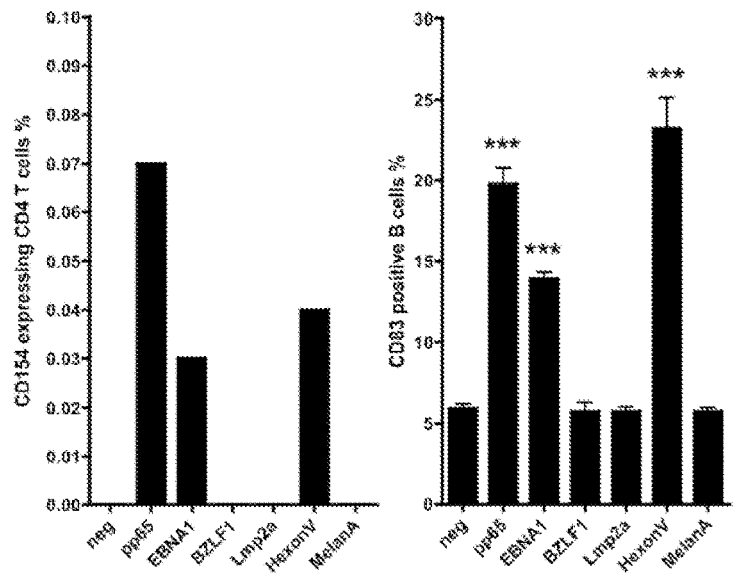
Figure 1C:
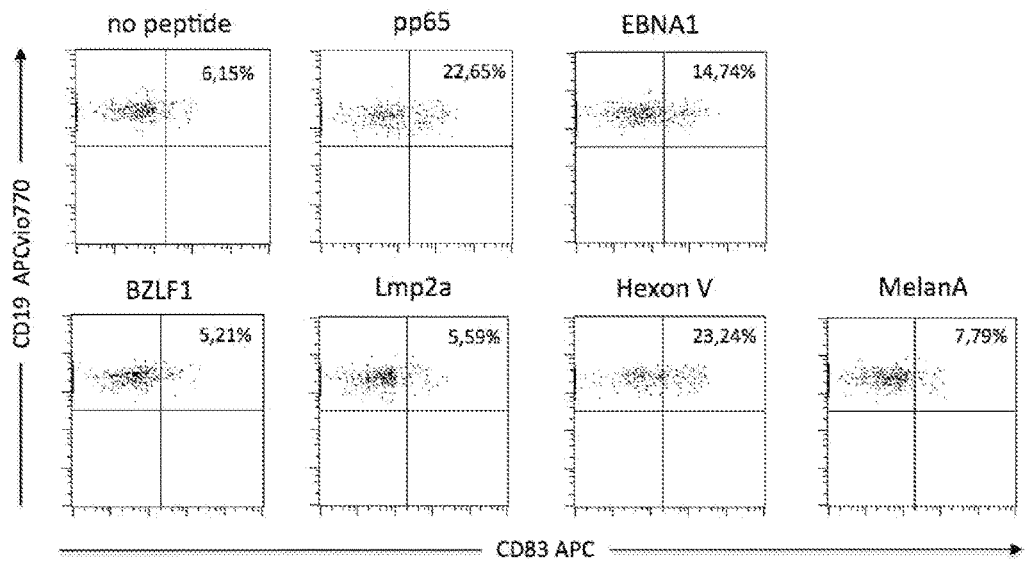
Figure 1D:
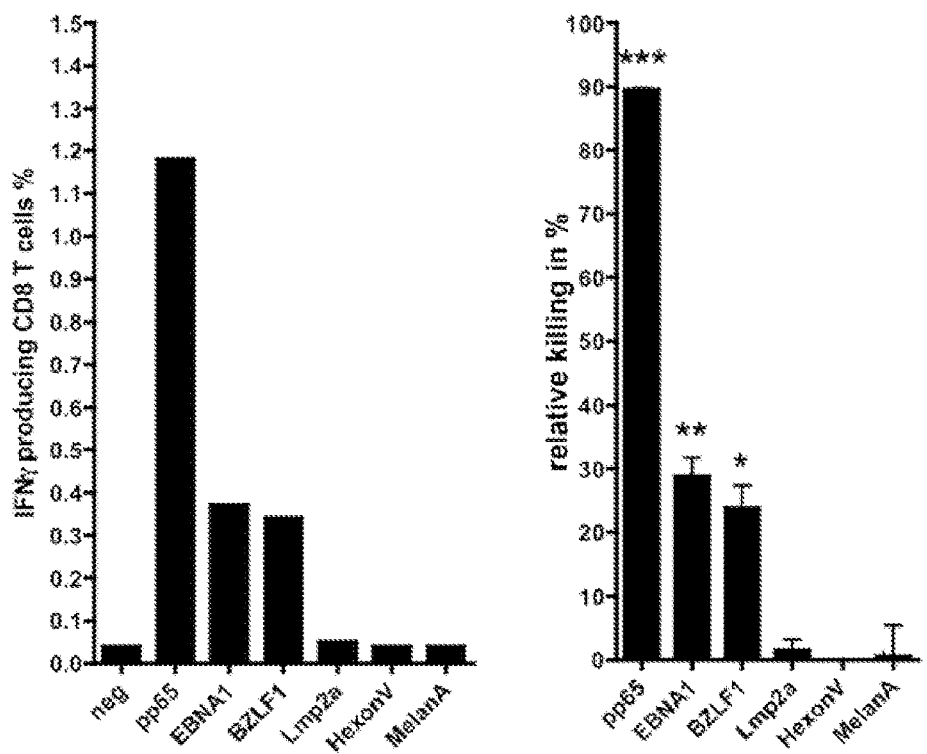
Figures 1E, 1F:
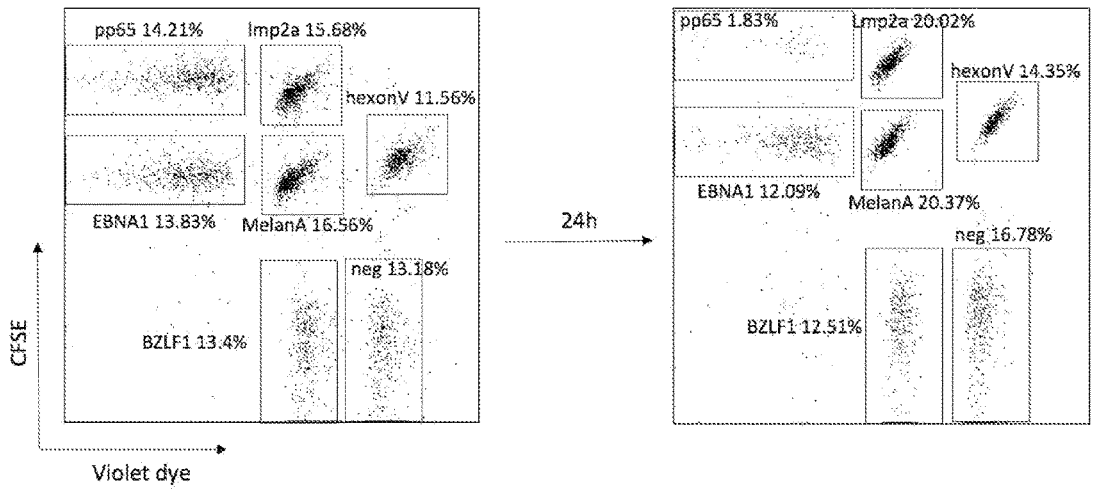
FIG. 1F. The formula to calculate cytotoxic killing is shown in the shaded field. The calculations of cytotoxic killing for pp65, EBNA1 and BZLF1 in (E) pulsed B cells are shown as examples.

The % specific killing is assessed based on the relative ratios of B cells present in the sample after and before sample incubation. Assuming that no specific B cell killing occurs in sample before incubation the ratio of the number of peptide-pulsed B cells to unpulsed B cells in the sample before incubation is defined as 0% killing. The value of the ratio between peptide-pulsed and unpulsed B cells should be identical in the sample after incubation if no killing occurs, but would decrease if killing has occurred. Therefore, comparing these ratios in samples after to samples before incubation, the % specific killing can be determined as shown in FIG. 1F.

CD4 ITRA

In another embodiment of the invention B cells are isolated untouched from a sample such as PBMC, divided into several sub-samples (at least 2) and incubated with different peptide pools. CD4 response already reached the maximum after 1 h of peptide pulsing. Using different combinations of cell dyes such as CFSE and violet dye, distinct populations of B cells can be acquired by flow cytometry. To display CD4 T cell antigen specificity CD4 T cells have to be separated from the remaining sample, i.e. CD8/CD19/CD56 depleted PBMC. These CD4 T cells and the with different peptides loaded B cells are co-cultured (optimally for 24 hours). Increased expression of CD83 was analyzed by flow cytometry comparing unpulsed and control peptide pulsed B cells with antigen peptide pool pulsed B cells to identify antigen specific interaction between CD4 T cells and B cells. Additionally, B cell populations are used to analyze killing of B cells by antigen-specific T cells. Relative specific killing was calculated comparing the ratio of % peptide pulsed B cell and the reference % B cells as described above (FIG. 1F). In an alternative embodiment of the invention CD4 T cells may be isolated positively by e.g. anti CD4 antibody labeled magnetic beads.

CD8 ITRA

In a further embodiment of the invention B cells are isolated untouched from a sample such as PBMC, divided into several sub-samples (at least 2) and incubated with different peptide pools. To achieve a full CD8 response B cells have to be incubated with peptides for at least 2 h (optimal incubation time depends on the length of peptide fragments presented). Using different combinations of intracellular fluorescence dyes, such as CFSE and violet dye, distinct populations of B cells can be acquired by flow cytometry. To display CD8 T cell antigen specificity CD4 T cells and NK cells have to be separated from the remaining sample, i.e. CD4/CD19/CD56 depleted PBMC. These CD8 T cells and the with different peptides loaded B cells are co-cultured (optimally for 24 hours). Increased expression of CD83 was analyzed by flow cytometry comparing unpulsed and control peptide pulsed B cells with antigen peptide pool pulsed B cells to identify antigen specific interaction between CD8 T cells and B cells. Additionally, B cell populations are used to analyze killing of B cells by antigen-specific T cells. Relative specific killing was calculated comparing the ratio of % peptide pulsed B cell and the reference % B cells as described above (FIG. 1F). In an alternative embodiment of the invention CD8 T cells may be isolated positively by e.g. anti CD8 antibody labeled magnetic beads.

CD20 B Cell Isolation

In another embodiment of the invention B cells are separated from a sample such as PBMC using magnetic columns for retaining the labeled B cells. To achieve the effect of retaining B cells magnetically in a column, the B cells are labeled before separation e.g. with magnetic microparticles coupled to CD20 antigen binding fragments. For dividing the sample into several B cell containing samples, the B cells are spread over several columns. The B cells on the columns are incubated with different peptide pools and labeled with intracellular fluorescent dyes as described above. Afterwards, the B cells are eluted from the columns (positive fraction).

Or B cells from PBMC or from blood are isolated via a single column or whole blood column, respectively. B cells are eluted and divided into samples for pulsing and labeling.

The negative fraction (flow through) contains the T- and other cells, excluding the B cells. The negative fraction may be separated into further subpopulations such as CD4 T cells, CD8 T cells and NK cells.

The negative fraction (containing all subpopulations of the original sample excluding B cells or the further processed sample resulting in a specific subpopulation of cells of the original sample) and differently peptide loaded B cells are co-cultured (optimally for 24 hours). Increased expression of CD83 was analyzed by flow cytometry comparing unpulsed and control peptide pulsed B cells with antigen peptide pool pulsed B cells to identify antigen specific interaction between T cells and B cells. Additionally, B cell populations are used to analyze killing of B cells by antigen-specific T cells. Relative specific killing was calculated comparing the ratio of % peptide pulsed B cell and the reference % B cells as described above (FIG. 1F).

NK Cell ITRA

In a further embodiment of the invention B cells are isolated untouched from a sample such as PBMC, divided into several sub-samples (at least 2) and incubated with different peptide pools. To achieve a full NK cell response B cells have to be incubated with peptides for at least 2 h (optimal incubation time depends on the length of peptide fragments presented). Using different combinations of cell dyes, such as CFSE and violet dye, distinct populations of B cells can be acquired by flow cytometry. To display NK cell antigen specificity CD4 and CD8 T cells have to be separated from the remaining sample, i.e. CD4/CD8/CD19 depleted PBMC. These NK cells and different peptides loaded B cells are co-cultured (optimally for 24 hours). Increased expression of CD83 was analyzed by flow cytometry comparing unpulsed and control peptide pulsed B cells with antigen peptide pool pulsed B cells to identify antigen specific interaction between NK cells and B cells. Additionally, B cell populations are used to analyze killing of B cells by antigen-specific T cells. Relative specific killing was calculated comparing the ratio of % peptide pulsed B cell and the reference % B cells as described above (FIG. 1F). In an alternative embodiment of the invention NK cells may be isolated positively by anti CD56 antibody labeled magnetic beads.

Without intending to be limiting, the invention will be illustrated with reference to the following examples.

EXAMPLES

Example 1

ITRA for CD4 T Cell Help

ITRA can be used to detect CD4 T cell help on B cells. To perform this assay, B cells were isolated from PBMC and incubated over night separately with different peptide pools. Using different combinations of CFSE and violet dye, 9 distinct populations of B cells can be acquired by flow cytometry (FIG. 1A). 1×10e6 CD8/CD19/CD56 depleted PBMC and 2×10e4 differently peptide loaded B cells were co-cultured for 24 hours. CD83 expression of each B cell population was measured by flow cytometry (FIG. 1C). Data of one representative donor is shown here as an example. We can observe a strong up regulation of CD83 for peptide pool pp65 and HexonV as well as a weaker signal for peptide pool EBNA1, whereas the value for all other antigen specificities remain at the background level (FIG. 1B). We did not detect CD83 up regulation, if the corresponding CD4 T cells were not present (FIG. 1B). Data of 3 independent samples is shown±SEM. *, $p<0.05$, , $p<0.001$ and *, $p<0.0001$ comparing peptide labeled B cells and peptide free B cells.

CD154 positive CD4 T cell frequencies (gated on CD4+ cells) were acquired by CD154 intracellular staining upon 6h stimulation of different PBMC samples with peptide pools.

Example 2

ITRA for CD8 T Cell Cytotoxicity

Also the CD8 T cell cytotoxicity can be displayed by ITRA. Here 1×10e6 CD4/CD19/CD56 depleted PBMC and 2×10e4 differently peptide loaded and subsequently bar-coded B cells were co-cultured for 24 hours. Relative specific killing was calculated comparing the ratio of peptide pulsed B cells and the reference B cells (peptide free B cells). One calculation example is shown (FIG. 1E, FIG. 1F) The investigated donor exhibited strong pp65 specific lysis and moderate EBNA1 and BZLF1 specific lysis (FIG. 1D right). This correlates to the frequency of IFNγ producing CD8 T cells of this donor (FIG. 1D left). Data of 3 independent samples is shown±SEM (*, $p<0.05$, , $p<0.001$ and *, $p<0.0001$ comparing relative killing of virus peptide labeled B cells and MelanA peptide loaded B cells). IFNγ positive CD8 T cell frequencies (gated on CD8+ cells) were acquired by IFNγ intracellular staining upon 6h stimulation of different PBMC samples with peptide pools.

Example 3

ITRA for CD4 T Cell Cytotoxicity

Figure 2A:
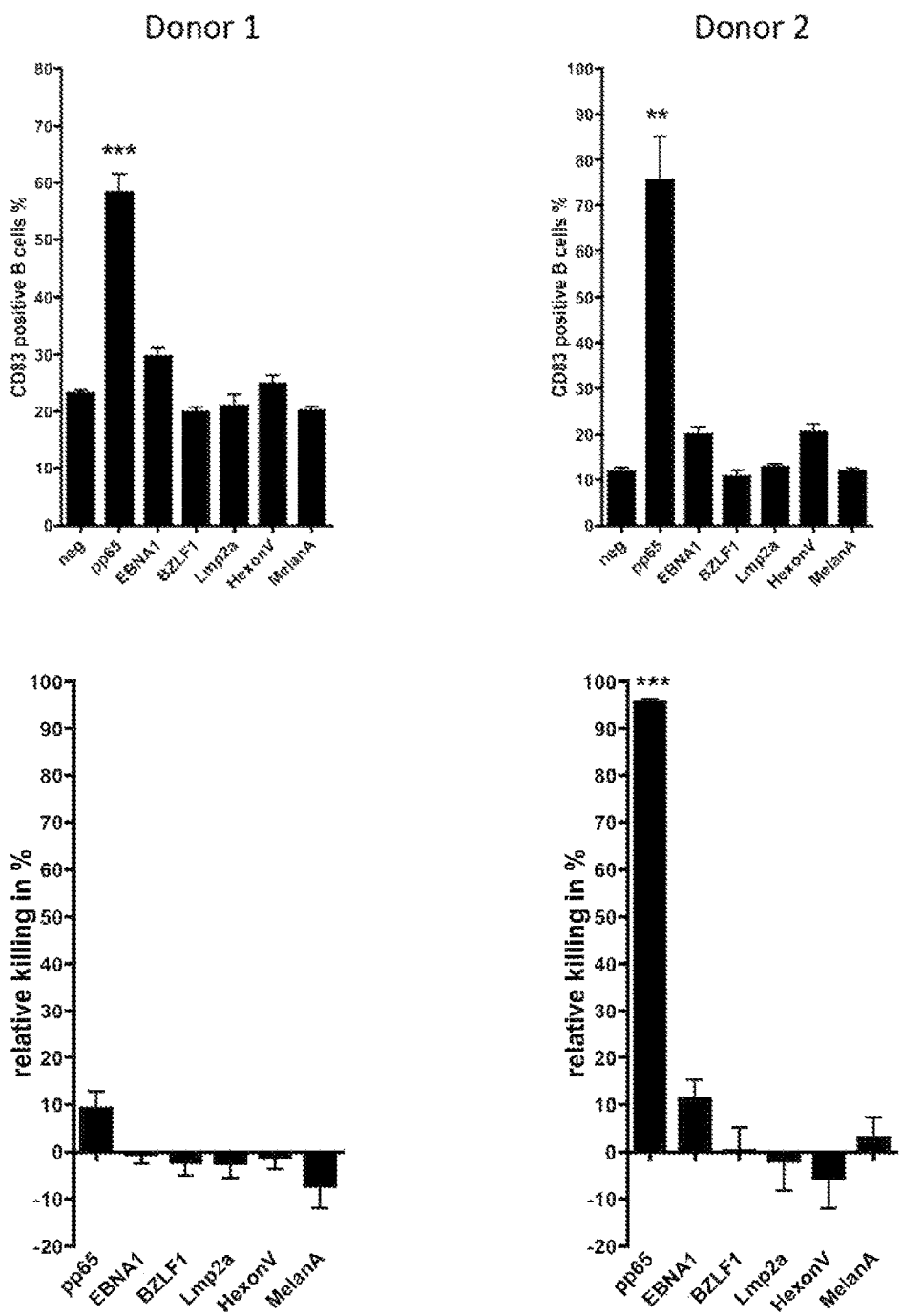
FIG. 2: A: Detection of cytotoxic CD4 T cells with ITRA. As in FIG. 1 using ITRA two donors (left and right diagrams) were analyzed for CD4 T cell cytotoxic activity and CD83 induction on peptide loaded and barcoded B cells as indicated. Donor 2 shows cytotoxic CD4 T cell activity against pp65 peptide loaded B cells (lower diagram) whereas donor 1 only shows CD83 expression on pp65 peptide loaded B cells but no cytotoxicity.
FIG. 2B: PBMCs were stimulated with pp65 for 6 h. Monensin and CD107a PE was added to the cultures at the start of the stimulation. IFNγ was stained intracellular after the stimulation. Cells were analyzed by flow cytometry and pre-gated on CD4 T cells.
Figure 2B:
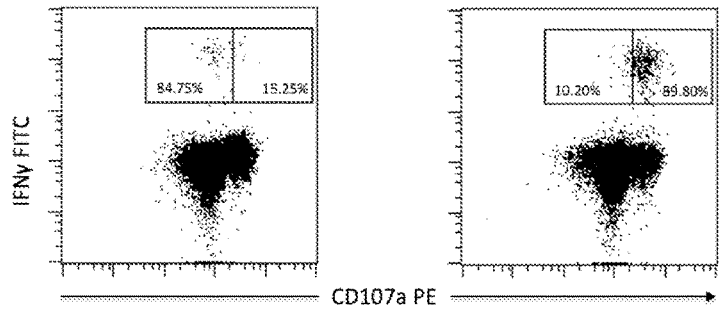

Not only CD8 but also CD4 cytotoxic T cells contribute to the clearance of different virus infections in mice and human. Also tumor-infiltrating CD4 T cells have been reported to mediate cytotoxicity against autologous carcinoma (Dorothee et al. 2002: J Immunol 169; 809-817). Since CD4 T cell cytotoxicity draw more and more attention for cellular therapies, interest rate has been raised also to characterize the killing ability of CD4 T cells for different Ag specificities. Here an ITRA assay was set up as described in Example 1. For instance, we observed 2 donors with similar profile of antigen specificities (FIG. 2A). Both donors exhibited reactivity for pp65 whereas only CD4 T cells from donor 2 clearly showed a strong cytotoxicity at the same time. This correspondently correlates to the intracellular CD107a expression of pp65 specific CD4 T cells as shown in FIG. 2B. Killing was calculated as described in Example 2. Data of 3 independent samples is shown±SEM. For CD83 analysis: , $p<0.001$ and *, $p<0.0001$ comparing peptide labeled B cells and peptide free B cells. For killing analysis: ***, $P<0.0001$ comparing relative killing of virus peptide labeled B cells and MelanA peptide loaded B cells.

Example 4

ITRA for NK Cell Cytotoxicity

Figure 4A:
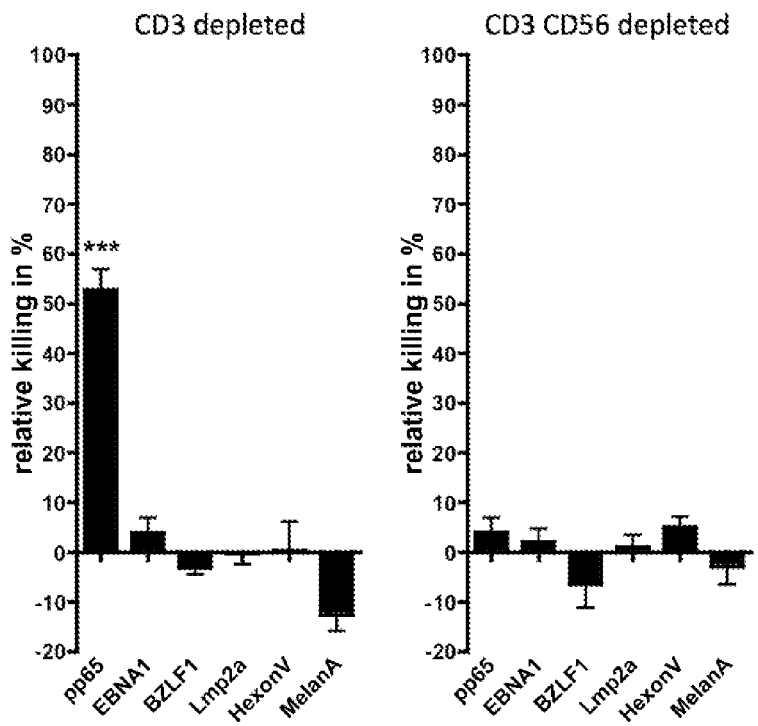
FIG. 4: Ag specific MHC-peptide dependent NK cell killing. ITRA was performed with NK cells instead of T cells. In absence of T cells two donors show killing of FIG. 4A. pp65 and FIG. 4B. BZLF1 loaded B cells (left diagrams). T cells were depleted by CD3. As control, the additional depletion of NK cells by CD56 (right diagrams) shows no killing in both donors.
FIG. 4C. Flow cytometric analysis of PBMC before and after depletion of T cells, or depletion of T cells and NK cells.
Figure 4B:
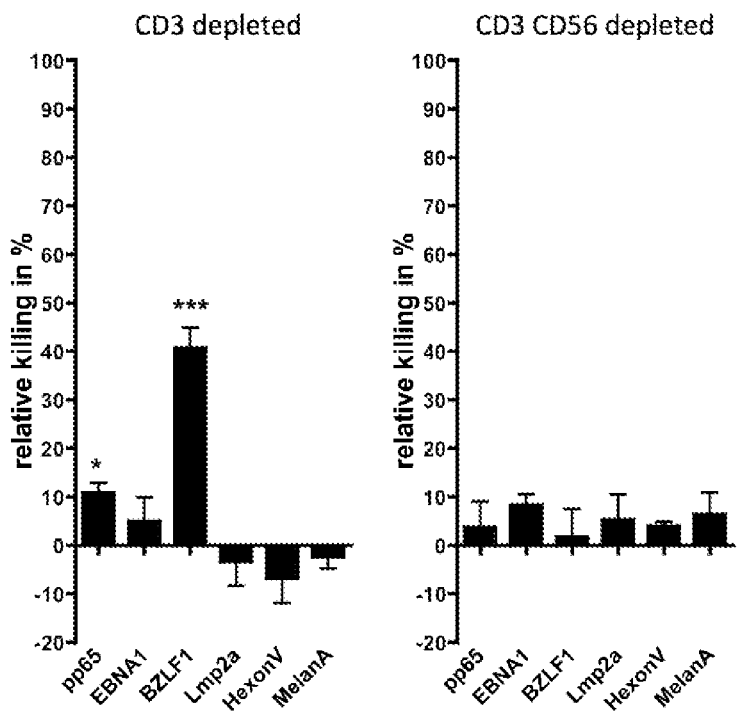
Figure 4C:
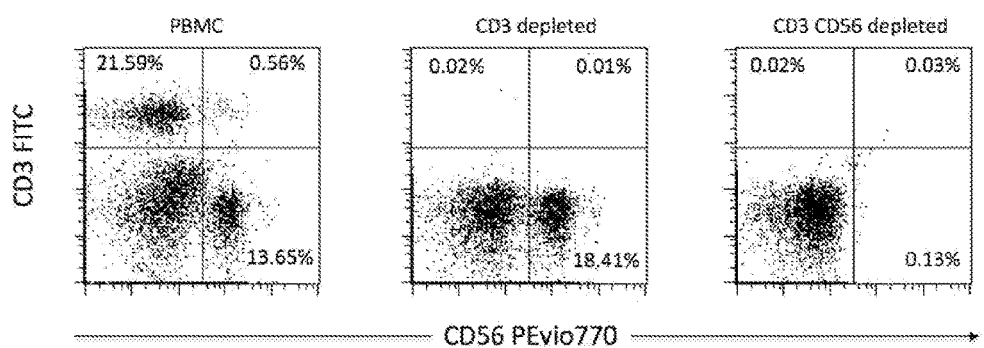

NK cell activation and inhibition is controlled by a balance of signals transduced from NK cell-activating receptors and inhibitory receptors specific for major histocompatibility complex class I molecules (MHC-I). Down regulation of MHCI expression (Ljunggren et al. 1990: Immunol Today 11:237-44) or expression of distinct virus protein lead to NK cell activation and target cell lysis (Sun et al. 2009: Nature 457:557-561; Mandelboim et al. 2001: Nature 409: 1055-60). However, MHC-peptide recognition by NK cell is not suggested because NK cells do not express TCRs. Recent bioinformatic analyses have demonstrated that NK cells are even more closely related to T cells than any other immune cell population (Robbins et al. 2008: Genome Biol. 9:R17; Yamagata et al. 2006: Immunol. Rev. 210:32). We performed ITRA with NK cells as effector cells. Here 1×10e6 CD3/CD19 depleted PBMC and 2×10e4 differently peptide loaded and subsequently bar-coded B cells were co-cultured for 24 hours. In FIG. 4A and FIG. 4B we show two donors with respective pp65 or BZLF1 specific NK cell killing. By additional depletion of CD56 positive cells, antigen specific killing was completed abolished. Killing was calculated as described in Example 2. Data of 3 independent samples is shown±SEM. $P<0.0001$ comparing relative killing of virus peptide labeled B cells and MelanA peptide loaded B cells.

Example 5

ITRA for CSA Isolated Cells as Clinical Application

Figure 5B:
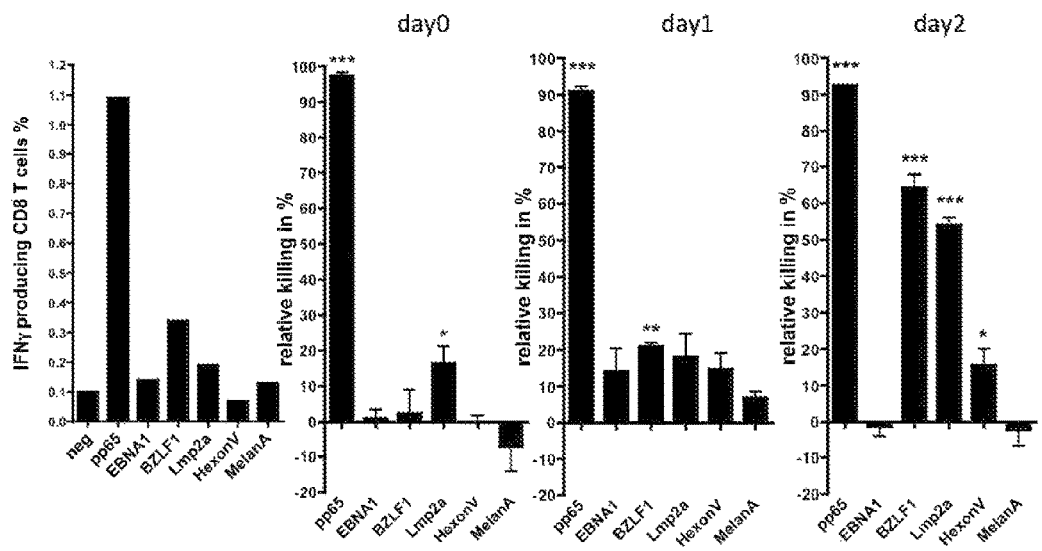
Figure 5C:
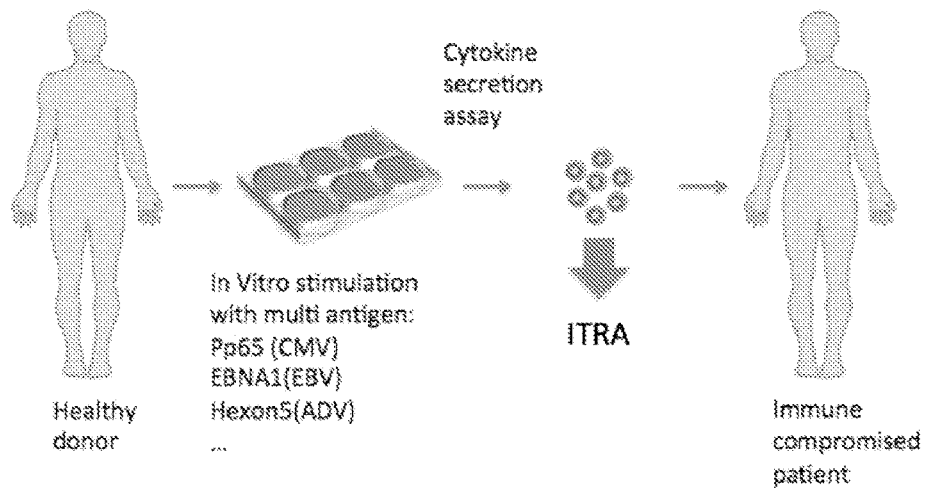

Opportunistic infection has become serious threat for immune compromised patients by inducing infection or triggering post-transplantation lymphoproliferative disease (PTLD) for example after allogeneic stem-cell transplantation (SCT). Besides anti-viral drug treatment, different cellular therapies have been developed. Virus specific T cells have been transferred from healthy donors to patients in order to provide them with protection against infections (Freuchtinger et al. 2010: Blood 116; 4360-67; Icheva et al. 2012: J Clin Oncol. 1; 31(1):39-48; Leibold et al. 2012: J immunther. 35; 9; 661-9). One of the most efficient approaches to acquire multiple virus specific T cells is to stimulate PBMC from proper donors with peptides of different pathogens and subsequently isolate the IFNγ producing cells using cytokine secretion assay (CSA). It is difficult to display and control antigen specificities of these isolated cells because they have been highly activated, have down regulated TCR on the cell surface and do not produce cytokine upon direct re-stimulation. Re-stimulation is only possible after a week of cultivation and high amount of cells are needed to perform multiple antigen stimulation in separate cultures. Using ITRA, CSA isolated cells can be characterized for their antigen specificities directly after isolation. We performed cytokine secretion assay (CSA) 4 h after stimulation of PBMC with multiple peptide pools. IFNγ producing CD8 T cells were highly enriched (FIG. 5A). 2×10e5 isolated cells were co-cultured with 2×10e4 differently peptide-pulsed and bar coded B cells for 24 h. Killing was calculated as described in Example 2. Strong pp65 specific cytotoxic killing was measured directly after isolation (FIG. 5B). After 2 days cultivation of isolated cells without addition of any cytokines, 2×10e5 cells from the culture were co-cultured with 2×10e4 freshly prepared B cells for 24 h. Significant killing for BZLF1 and Lmp2a were detected, indicating a proliferation of these T cells during the cultivation. This kind of characterization could provide valuable information to predict the outcome of cell transfer therapies at an early time point (FIG. 5C).

The invention claimed is:

1. A method for analyzing simultaneously multiple human antigen-specific cell populations of a sample, the sample comprising B cells and antigen-specific cells, the method comprising
   a) separation of B cells from said sample
   b) dividing the B cells into n sub-samples c) differentially labeling the B cells of said sub-samples, wherein at least n-1 sub-samples are labeled
d) pulsing of the B cells of each sub-sample with single or multiple peptides
e) pooling of the labeled and peptide-pulsed B cells with cells of said sample comprising said antigen-specific cells of step a)
f) co-cultivation of the cells of step e)
g) flow cytometry analysis of the B cells with regard to their cell number and/or CD83 expression loaded with single or multiple peptides of step d), wherein the potency of the antigen specific cells is determined by
i) B cell numbers if extensive killing of target B cells occurs,
ii) B cell numbers and ratio of CD83 expression on survived target B cells if moderate killing of target B cells occurs, or
iii) ratio of CD83 expression on target B cells if no cytotoxic activity occurs.

2. The method of claim 1, wherein in step b), additionally to the separation of the B cells, said antigen-specific cells of said sample are separated into CD4 T cells, CD8 T cells or NK cells.

3. The method of claim 1, wherein the B cells in step c) are labeled with single or multiple fluorescent dyes in different concentrations and/or combinations thereof.

4. The method of claim 1 further comprising estimating the prognosis of adoptively T cell therapy, wherein the potency of the antigen specific cells indicates the prognosis of the adoptive T cell therapy.

* * * * *